United States Patent [19]
Watson et al.

[11] Patent Number: 5,328,362
[45] Date of Patent: Jul. 12, 1994

[54] SOFT RESILIENT INTEROCCLUSAL DENTAL APPLIANCE, METHOD OF FORMING SAME AND COMPOSITION FOR SAME

[76] Inventors: Sherman L. Watson, 12716 NE. 7th Pl., Vancouver, Wash. 98684; Jimmie J. Jones, 4416 SE. 34th St., Portland, Oreg. 97202; Richard W. Moore, 2103 NW. 272nd Ave., Camas, Wash. 98607

[21] Appl. No.: 849,467

[22] Filed: Mar. 11, 1992

[51] Int. Cl.$^5$ .............................................. A61C 3/00
[52] U.S. Cl. ........................................ 433/6; 128/861; 523/115; 523/120
[58] Field of Search ............... 523/115, 120; 433/6; 128/861, 862

[56] References Cited

U.S. PATENT DOCUMENTS

| | | |
|---|---|---|
| 368,492 | 8/1887 | Robinson ............. 433/200.1 |
| 583,307 | 5/1897 | Kleinert ............. 433/168.1 |
| 1,750,619 | 3/1930 | Bradley . |
| 2,057,341 | 10/1936 | Morgan ............. 433/168.1 |
| 2,165,597 | 7/1939 | Widoe ............. 32/2 |
| 2,457,114 | 12/1948 | Amenta ............. 264/338 X |
| 2,479,780 | 8/1949 | Remensnyder ............. 433/6 |
| 2,531,222 | 11/1950 | Kesling ............. 433/6 |
| 2,706,478 | 4/1955 | Porter ............. 128/862 |
| 2,789,351 | 4/1957 | Gordon ............. 264/16 X |
| 2,848,750 | 8/1958 | Sannecke et al. ............. 18/55.1 |
| 2,859,088 | 11/1958 | Erdle et al. ............. 264/18 |
| 2,874,466 | 2/1959 | Schnell ............. 32/2 |
| 2,934,823 | 5/1960 | Preis ............. 433/168.1 |
| 3,073,300 | 1/1963 | Berghash ............. 128/862 |
| 3,226,826 | 1/1966 | Town ............. 433/168.1 |
| 3,250,272 | 5/1966 | Greensberg ............. 128/862 |
| 3,303,844 | 2/1967 | Johnson et al. ............. 264/16 |
| 3,319,626 | 5/1967 | Lindsay ............. 433/6 X |
| 3,404,056 | 10/1968 | Baldwin ............. 264/16 |
| 3,768,164 | 10/1973 | Breads ............. 433/37 X |
| 3,898,683 | 8/1975 | Breads ............. 95/1.1 |
| 3,969,303 | 7/1976 | Prosen ............. 433/168.1 X |
| 4,012,838 | 3/1977 | Abdenour ............. 32/2 |
| 4,024,636 | 5/1977 | Colpitts et al. ............. 32/2 |
| 4,044,762 | 8/1977 | Jacobs ............. 433/6 X |
| 4,080,412 | 3/1978 | Colpitts et al. ............. 264/17 X |
| 4,112,023 | 9/1978 | Gore et al. ............. 264/16 X |
| 4,161,065 | 7/1979 | Gigante ............. 264/18 X |
| 4,251,215 | 2/1981 | May et al. ............. 433/168 |

(List continued on next page.)

Primary Examiner—Gene Mancene
Assistant Examiner—Nicholas D. Lucchesi
Attorney, Agent, or Firm—Kolisch, Hartwell, Dickinson, McCormack & Heuser

[57] ABSTRACT

A unitary plural-material, interocclusal dental appliance is disclosed for use in connection with orthodontic/orthopedic treatment of the teeth and jaws of a patient's mouth. The appliance includes a first region made from a first material that provides a relatively hard expanse with first and second surfaces, and with the second surface being contactable by one such set of teeth. The second surface may be constructed with a substantially planar shape, or with a shape conforming generally to the cusps of such one set of teeth. A second region is joined to the first region, and is made from a second material that provides a relatively soft, persistently resilient enclosure for the other such set of teeth. The second region includes plural zones, each of which is structured to allow an adjacent enclosed tooth to move toward the first surface of the first region, with such movement resulting in penetration of corresponding teeth into the relatively hard first material for a relatively precise distance. Such penetration defines lateral borders in the first material around such teeth so that the appliance accommodates relatively fixed vertical and lateral positioning of the mandible by enclosing such teeth upon desired biting action by the patient. A method for forming such appliance is also disclosed. Additionally, a curable composition for making a soft, persistently resilient dental appliance is disclosed and it includes a polymer component including butyl methacrylate polymer, and a monomer component including butyl methacrylate monomer.

22 Claims, 3 Drawing Sheets

U.S. PATENT DOCUMENTS

| | | | |
|---|---|---|---|
| 4,304,227 | 12/1981 | Samelson | 128/136 |
| 4,448,735 | 5/1984 | Huge | 264/16 |
| 4,543,379 | 9/1985 | Gettleman et al. | 433/168.1 X |
| 4,568,280 | 2/1986 | Ahlin | 433/6 |
| 4,579,881 | 4/1986 | Masuhara et al. | 433/168.1 X |
| 4,580,981 | 4/1986 | Bannai et al. | 433/168.1 X |
| 4,634,381 | 1/1987 | Kusano et al. | 433/168.1 X |
| 4,654,006 | 3/1987 | Kusano et al. | 433/168.1 X |
| 4,661,065 | 4/1987 | Gettleman et al. | 433/168.1 X |
| 4,755,139 | 7/1988 | Abbatte et al. | 433/6 |
| 4,798,534 | 1/1989 | Breads | 433/6 |
| 4,856,991 | 8/1989 | Breads et al. | 433/6 |
| 4,873,269 | 10/1989 | Nakazato | 523/115 |
| 4,920,984 | 5/1990 | Furumichi et al. | 433/6 X |
| 4,983,334 | 1/1991 | Adell | 264/16 |
| 4,988,291 | 1/1991 | Grummons | 433/5 |
| 5,035,613 | 7/1991 | Breads et al. | 433/6 |
| 5,037,473 | 8/1991 | Antonucci et al. | 433/168.1 X |
| 5,055,039 | 10/1991 | Abbatte et al. | 433/24 |
| 5,059,118 | 10/1991 | Breads et al. | 433/24 X |

SOFT RESILIENT INTEROCCLUSAL DENTAL APPLIANCE, METHOD OF FORMING SAME AND COMPOSITION FOR SAME

BACKGROUND AND SUMMARY OF THE INVENTION

The invention relates generally to dental appliances and synthetic compositions used to make them. More particularly, the invention concerns an improved interocclusal appliance which provides improved appliance retention and precise vertical and lateral positioning of the mandible, as well as a method of forming such appliance, and a curable composition for making dental appliances such as the invented appliance.

Interocclusal appliances, commonly referred to as splints, are well known, and are used to secure or hold in proper position (or desired range of positions) the mandible of a patient. Splints may be used for orthodontic treatment, as well as for orthopedic treatment of the bone, joints and supporting tissue associated with the mouth.

For example, splints are used to treat various conditions including temporomandibular joint (TMJ) dysfunction syndromes, myofascial pain dysfunction syndrome, and symptomatic or asymptomatic loss of tooth structure from subconscious parafunctional mandibular habits known as bruxism (grinding) or clenching. Splints are also used to reduce wear on teeth caused by metal or porcelain dental restorations during normal, functional or parafunctional mandibular movement. Splints may also be used as antisnoring devices to resolve snoring problems and obstructive sleep apnea (OSA).

Several unimaterial, conventional splints have been proposed but there are certain problems common to all of them. First, none of the so-called "soft" splints remain soft over time. Conventional splints harden over time due to their composition and/or due to leaching out of unreacted plasticizers present in them. Such hardening is a drawback because soft, resilient splints are preferred. Soft splints are preferred because they are more comfortable to wear than hard appliances, and because they provide improved retention of the splint held by the teeth.

A second drawback associated with such splints is that they are notoriously imprecise in terms of vertical and lateral positioning of the mandible under desired patient-bite conditions before they harden. Precise vertical and lateral positioning of the mandible is critical to proper orthodontic/orthopedic treatment. The section of conventional soft splints that is sandwiched by opposing sets of teeth is imprecise because it "gives" an irregular amount when the patient bites down under normal pressure, resulting in reduced TMJ stability in all dimensions.

Certain proposals have been made to make splints and other dental appliances out of two materials with differentiated hardnesses. Apparently, the idea is to use harder material in such appliances where harder material is needed and softer material where it is needed. For example, such proposals have been made in U.S. Pat. No. 4,448,735 to Huge, U.S. Pat. No. 3,404,056 to Baldwin, U.S. Pat. No. 2,934,823 to Preis and U.S. Pat. No. 2,789,351 to Gordon. However, none of the prior art proposals has been effective in overcoming the above-identified problems for splints.

Accordingly, it is a principal object of the present invention to provide an improved composition for a soft, persistently resilient, interocclusal dental appliance.

Another object is to provide such a composition that can be used for a dental appliance to impart in it the characteristic of being relatively soft and persistently resilient at mouth temperature for the working life of the appliance.

Yet another object is to provide an improved splint that adequately grasps the teeth of the user while also precisely retaining the mandible and/or TMJ in a desired position.

Another important object of the invention is to provide an improved splint that accommodates an immediate and accurate fit with the desired set of teeth jacketed by it and with the opposing set of teeth in contact with it.

Still another object is to provide an improved dental appliance that is comfortable to wear.

Yet another object is to provide a method of forming a plural-material interocclusal dental appliance from a unimaterial version of such appliance.

It is also an object of the invention to provide such an appliance that can be easily and cost-effectively manufactured.

In brief summary, one aspect of the invention includes a unitary plural-material, interocclusal dental appliance for use in connection with orthodontic/orthopedic treatment of the teeth and jaws of a patient's mouth. The appliance includes a first region made from a first material that provides a relatively hard, expanse with first and second surfaces, with the second surface being contactable by one such set of teeth. The second surface may be constructed with a substantially planar shape or with a shape that conforms generally to the cusps of such one set of teeth. A second region is joined to the first region, and is made from a second material that provides a relatively soft, persistently resilient enclosure for the other such set of teeth.

The second region includes plural zones, each of which is structured to allow an adjacent enclosed tooth to move toward the first surface of the first region, with such movement resulting in penetration of corresponding teeth into the relatively hard first material for a relatively precise distance. Such penetration defines lateral borders in the first material around such teeth so that the appliance accommodates relatively fixed lateral and vertical positioning of such enclosed teeth upon desired biting action by the patient.

Another aspect of the invention is a curable composition for making a soft, persistently resilient dental appliance. The composition includes a polymer component including butyl methacrylate polymer, and a monomer component including butyl methacrylate monomer. The soft, persistently resilient appliance formed from the composition of the present invention offers increased patient comfort and improved tooth retention.

Another aspect of the invention is a method of forming a unitary plural-material, interocclusal dental appliance for use in connection with orthodontic/orthopedic treatment of the teeth, jaws and mandible of a patient's mouth. The method is used in connection with conventional molding techniques usable to form a unimaterial interocclusal dental appliance in a corresponding cavity of a mold. The method of the invention includes the steps of (1) removing a first section of such conventionally formed unimaterial appliance to expose a surface of a second section of it, (2) putting such unimaterial appliance back in the mold so that a void is formed, the void being defined by the removed first section, (3) filling the void with curable material that is different from the material used to form such unimaterial appliance, and (4) curing the newly formed appliance so that the two materials bond together along the surface of the second section, thus to form a unitary plural-material, interocclusal dental appliance with the first section made from material that is different from the second section.

These and other objects and advantages of the invention will be more clearly understood from a consideration of the accompanying drawings and the following description of the preferred embodiment.

BRIEF DESCRIPTION OF THE DRAWINGS

In the interest of clarity, it will be appreciated that the preferred embodiment of the invention is illustrated and described consistently, with respect to orientation, relative to its use in a patient's mouth. Thus, the orientation of the dental appliance illustrated in FIGS. 1 through 6 is described using anatomical terminology, as though the appliance were positioned in the mouth.

DETAILED DESCRIPTION OF THE PREFERRED EMBODIMENT

Figure 1:
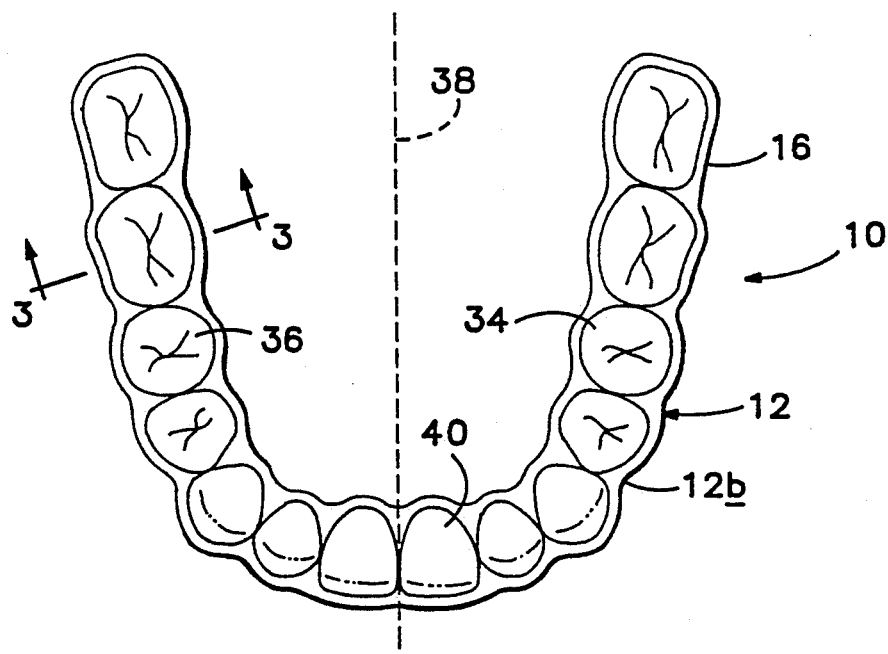
FIG. 1 is a top view of the preferred embodiment of the invention which is in place in the mouth of a patient, showing the upper teeth of the patient located in the appliance but blocking out all remaining portions of the mouth.
Figure 2A:
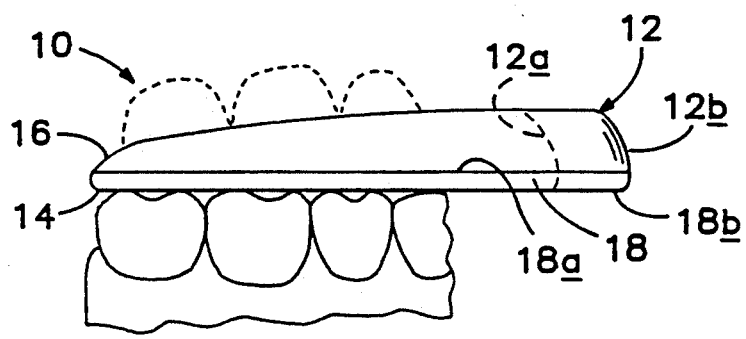
FIG. 2A is a right, buccal side view of the preferred embodiment of the invention shown in FIG. 1 with certain portions of the mouth shown.

FIGS. 1 and 2A depict top and side views of the invented unitary, plural-material interocclusal dental appliance, made in accordance with its preferred embodiment and indicated at 10. Preliminarily, it should be understood that appliance 10 may also be thought of as a TMJ dysfunction appliance. As will be understood, appliance 10 may be used by a patient for orthodontic-/orthopedic treatment of the teeth, joints and bone associated with a patient's mouth.

Focusing first on FIG. 1, appliance 10 preferably has a generally U-shaped body 12. The inner U-shaped border 12a of body 12 corresponds to the tongue or lingual side of the appliance and the outer U-shaped border 12b corresponds to the cheek or buccal side of the appliance.

Figure 2B:
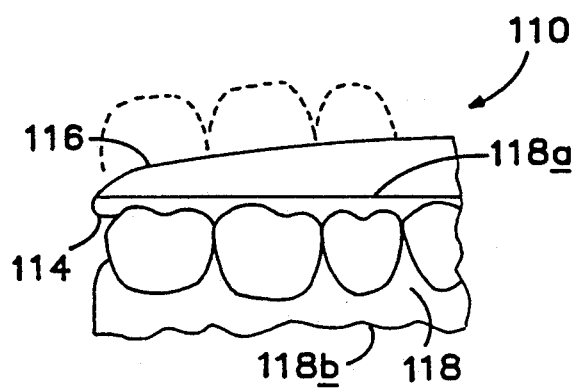
FIG. 2B is a right, buccal side view similar to FIG. 2A only showing a second embodiment of the invention.
Figure 3:
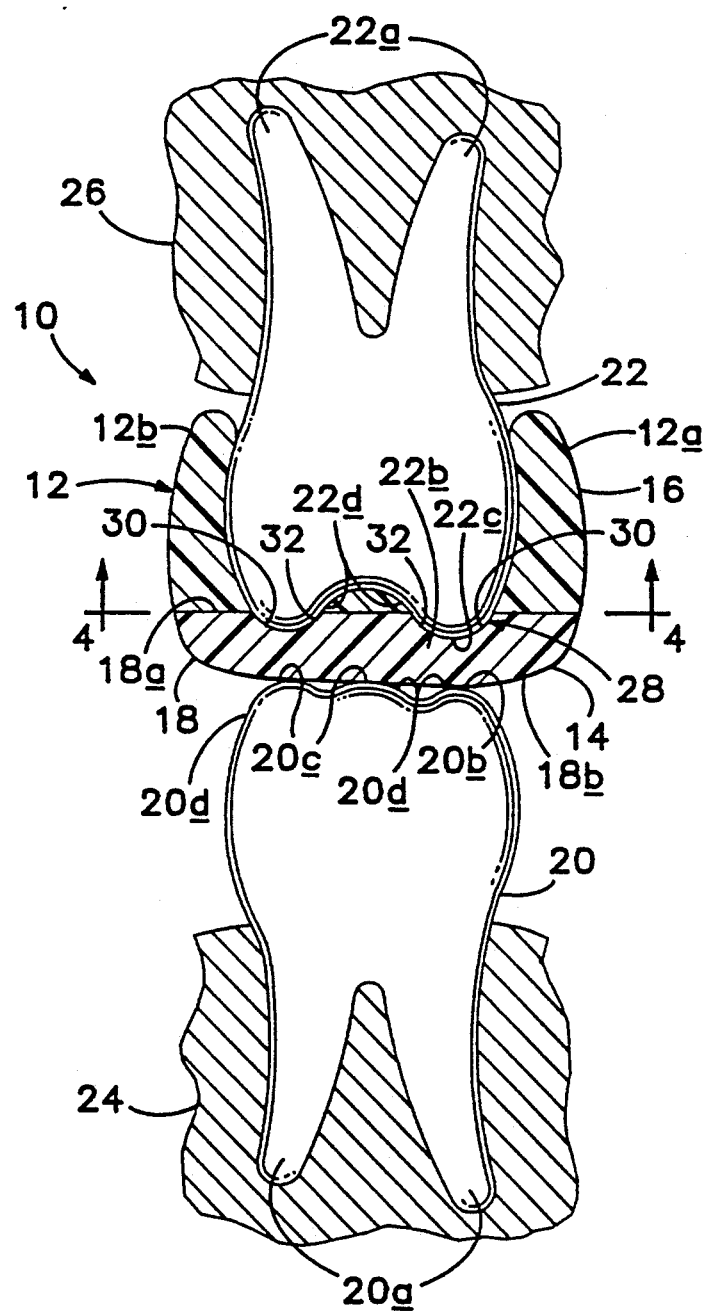
FIG. 3 is a fragmentary sectional view through line 3—3 of FIG. 1 which also shows portions of the gums and jaw of the mouth as well as a pair of opposing teeth.

Referring to FIGS. 2-3, body 12 includes a first region 14, also referred to as an occlusal layer or a relatively hard occlusal layer, joined to a second region 16, also referred to as a jacketing section. Further discussion of techniques for forming body 12 will follow soon. As for joinder of the two regions, such joinder may be accomplished by any suitable method such as by bonding them together. First region 14 is formed from a first material and second region 16 is formed from a second material, and both materials will be more particularly described below.

Referring to FIGS. 2A and 3, first region 14 takes the form of an expanse 18 with first and second surfaces 18a, 18b, respectively. Preferably, expanse 18 is constructed with a substantially planar second surface 18b but, as shown in FIG. 2B, a second embodiment of the invention is shown as an appliance 110 which includes expanse 118 being formed with a second surface 118b that conforms to the cusps of the lower teeth. The significance of constructing second surface 118b to conform with the cusps of the lower teeth will be described below.

Referring again to FIG. 3, second surface 18b is contactable by one set of teeth, such as the patient's lower teeth, one of which is shown at 20 in FIG. 3. Second region 16 takes the form of an enclosure (or jacketing section) for the patient's opposing set of teeth, such as the upper teeth, one of which is shown at 22. It should of course be understood that appliance 10 may be formed so that the jacketing section is usable on either the upper or lower set of teeth. Referring to teeth 20 and 22, each includes corresponding roots 20a, 22a which are shown positioned in lower and upper jaws 24, 26, respectively. Each tooth also includes corresponding cusps 20b, 22b. Each cusp may be thought of as having a top 20c, 22c and sides 20d, 22d, respectively.

Figure 4:
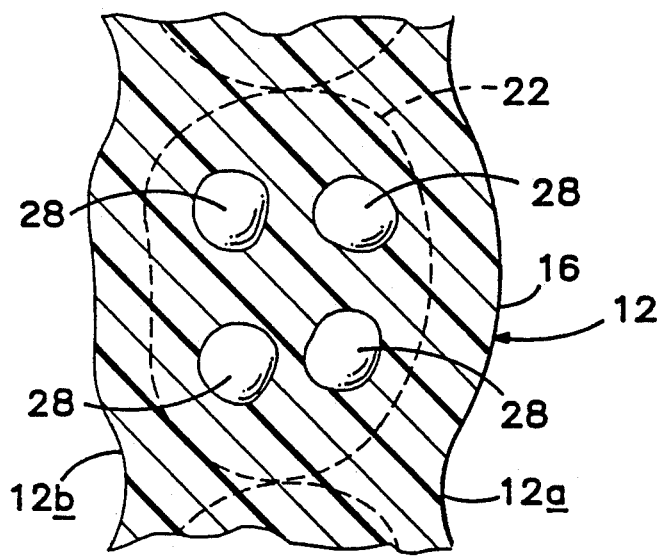
FIG. 4 is a sectional view through lines 4—4 of FIG. 3.
Figure 5:
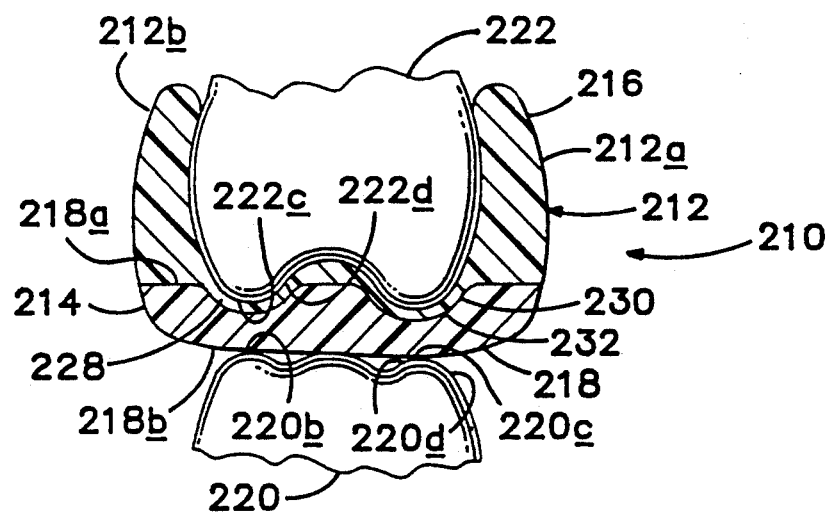
FIG. 5 is like FIG. 3 only slightly more fragmentary and showing a third embodiment of the invention.

Referring to FIGS. 3-4, one can see that second region 16 is formed with plural zones 28 which preferably take the form of openings that allow cusps 22b to contact first surface 18a of first region 18. Zones 28 may also be thought of as means for providing communication between selected ones of jacketed teeth (such as tooth 22 of FIG. 3) and first surface 18a of planar expanse 18. Referring for a moment to FIG. 5, a third embodiment of appliance is shown at 210 which includes plural zones 228 formed as relatively thin sections, i.e. with a thickness of about 0.5 mm-1.0 mm.

Referring to FIGS. 3 and 5 zones 28 and 228 each allow cusps 22b, 222b, to penetrate into first region 14, 214, respectively. Such penetration will be discussed further, but first it is important to understand certain details about the first and second material from which first and second regions 14, 16 (FIG. 3) are formed, respectively.

Referring again to FIGS. 1-3, first region 14 may be formed of any suitable relatively hard material that will allow teeth to penetrate into it only a relatively small, yet precise amount. Preferably, the first material is formed from known curable, acrylic-based polymer formulations that are commonly used in the field of orthodontics, such as polymethyl methacrylate (PMMA). PMMA, when cured, has a hardness that is greater than the to-be-described second material which is used to form second region 16.

Still referring to FIGS. 1-3, second region 16 is formed from a second material which forms another aspect of the present invention. This second material is characterized by a curable composition that is usable to make a soft, persistently resilient dental appliance. The composition includes a polymer component including butyl methacrylate polymer, and a monomer component including butyl methacrylate monomer. Preferably, the polymer component is about 20-80% by volume of the composition.

One example of a suitable composition for the second material is:

EXAMPLE 1

| Butyl Methacrylate polymer (BMA—P) | 10 g (9.35 ml) |
| Butyl Methacrylate monomer (BMA—M) | 13.4 ml |
| Benzoyl Peroxide | 0.2 g (0.15 ml) |

The butyl methacrylate polymer (BMA-P) is available from E.I. Du Pont de Nemours & Co., Inc. and is marketed under the trademark ELVACITE 2044. The butyl methacrylate monomer (BMA-M) is available from Rohm and Haas Co. Benzoyl peroxide is available from Spectrum Chemical Mfg. Corp. of Gardena, Calif.

The above example composition may be mixed with suitable mixing means and, once mixed, is in a liquid state. A suitable mold may be formed using conventional processes such as those disclosed in U.S. Pat. No. 4,654,006 to Kusano et al., U.S. Pat. No. 4,080,412 to Colpitts et al. and U.S. Pat. No. 2,859,088 to Erdle et al., which patents are incorporated herein by reference. The liquid composition is injectable into the mold cavity by using a suitable syringe with suitable pressure, and then a curing operation is followed to form the desired appliance.

The newly formed appliance is persistently resilient based on in-mouth aging tests performed on appliances made from the above-described curable composition. Such tests gave the following results:

|  | Appliance A | Appliance B |
| --- | --- | --- |
| Age | 3 wks. old - unused | 52 wks. old - used |
| Hardness* | 68.8 (73° F.) | 68.8 (73° F.) |
| (Shore D) | 58.8 (99° F.) | 59.2 (99° F.) |

*Hardness readings for the above tests were averaged from seven readings taken at random locations.

Prior to forming the unitary, plural-material interocclusal appliance of the present invention, certain conventional steps are followed and then certain novel steps are also performed, the latter forming another aspect of the invention. The conventional steps involve the usual unimaterial dental-appliance-molding techniques disclosed in the above patents. These conventional techniques are also known as a "lost wax" method of forming a dental appliance.

Briefly, the techniques involve forming a suitable cavity in a mold (also called a flask) that corresponds to the shape of the desired splint. A wax pattern of the splint is formed and placed in a desired position on a stone impression of a desired set of the patient's teeth. Then, the impression and wax pattern are placed in a suitable mold with sprues, which is then filled with a suitable material, such as a hydrocolloid material. Thereafter, the mold is put in a heated water bath to boil out the wax pattern and also to solidify the hydrocolloid material. The resulting mold includes a cavity that defines the desired splint.

The novel steps of the invention include certain improved steps practiced in connection with the above conventional molding techniques. The above conventional techniques are usable to form a unimaterial interocclusal dental appliance in the corresponding cavity of the mold. The improved steps are practiced to form a unitary plural-material, interocclusal dental appliance from such unimaterial one.

From an overview, the method of the invention involves (1) removing a first section of the conventionally formed unimaterial interocclusal dental appliance to expose a surface of a second section of it, (2) putting such unimaterial appliance back in the mold so that a void is defined by the removed first section, (3) filling the void with curable material that is different from the material used to form such unimaterial appliance, and (4) curing the newly formed appliance so that the two materials bond together along the surface of the second region, thus to form a unitary plural-material, interocclusal dental appliance with the first section made from material that is different from the second section.

Now focusing on further details of the method, after conventionally forming and curing the unimaterial appliance it is removed from the mold and cooled. Such appliance would have the appearance of appliance 10 of FIGS. 1, 2A and 3, only that it would be made solely of one material (such as the above-identified novel composition) instead of being made of two materials with corresponding regions like regions 14, 16. If the above-identified novel composition is used, it may be injected into the mold via the sprues and cured by placing the filled mold in a heated water bath (160° F.) for about two hours at 20 p.s.i.

It should be understood that appliance 10 in FIG. 3, which is a finished product, is now being used to further detail the steps used to practice the method of the invention. Generally, such steps involve forming a plural-material appliance (appliance 10) from a unimaterial appliance (undepicted). With reference to FIG. 3, imagine that it depicts a fragmentary section of stone teeth and gums, and a unimaterial appliance fitted on the upper stone teeth, all of which reside in a conventional mold (undepicted). Such unimaterial appliance would look like appliance 10 of FIG. 3 except that it would be unimaterial instead of having two regions 14, 16 made from different materials. Next, according to the method of the invention, the unimaterial appliance would be removed from the mold and a first section of it (corresponding to first region 14) would be removed with a suitable cutting device to expose a surface in a second section of it (corresponding to second region 16). Such exposed surface would correspond to the second-region side of the interface between first and second regions 14, 16 in FIG. 1. The result of such removal step would be to form zones in the unimaterial appliance like zones, or openings, 28 (FIGS. 3 and 4).

Then, the remainder of such unimaterial appliance is put back in the mold and a void is formed being defined by the just removed section of the appliance. For example, again referring to FIG. 3, the just cut unimaterial appliance would be put back in the mold in a position like that of appliance 10 with region 16 jacketing upper teeth such as tooth 22. However, the just cut unimaterial appliance would not have a section corresponding to region 14 because that would have been removed by the removing step. Next, suitable liquid PMMA is injected into the conventional mold (undepicted) via sprues to fill the void. Such liquid does not flow up through the openings in the surface of the second region because the stone teeth block such flow. To understand such relative positioning of the stone teeth and second section, FIG. 3 is again used to illustrate that the stone teeth would be positioned like upper tooth 22, which is seated in region 16 (corresponds to the second section of the unimaterial appliance). The cusps of tooth 22 block holes 28 by covering them.

Continuing with the description of the method of the invention, the conventional acrylic-based polymer in the mold is cured and the product is demolded using conventional procedures. The product is characterized by having a first region made from the above-described, relatively hard first material (see region 14 of FIG. 3) joined, or bonded, to a second region made from the above-described soft, persistently resilient second material (see region 16 of FIG. 3).

To achieve an even greater bond between the two regions, a suitable bonding agent may be applied to the surface that was exposed by the removing step prior to placing the unimaterial appliance back in the mold for injection of the liquid PMMA.

Turning now to FIGS. 3-5, it will be appreciated that zones 28 (FIG. 3)/128 (FIG. 5) allow an adjacent enclosed tooth, such as tooth 22 (FIG. 3)/128 (FIG. 5), to move toward first surface 18a (FIG. 3)/118a (FIG. 5) of first region 14 (FIG. 3)/114 (FIG. 5). Such movement results in penetration of corresponding teeth such as tooth 22/122 into the relatively hard first material of first region 14/114 for a relatively precise distance. Such penetration defines lateral borders in the first material, such as those shown at 30, around such teeth. The result of both such types of tooth movement toward expanse 18 and such lateral-border formation is that appliance 10/110 accommodates relatively fixed vertical and lateral positioning of the mandible by enclosing teeth such as tooth 22/122.

Put another way, and referring to FIG. 3 only, zones 28 allow advancement of cusps 22b into first surface 18a, thereby to form a pocket 32 in the first surface whose shape conforms generally to the cusp and has dimensions spanning top 22c of the cusp and at least part way down sides 20d of the cusp. With such cusp advancement and pocket formation defining lateral borders 30 in the first material of first region 14 around such teeth, the appliance accommodates relatively fixed lateral and vertical positioning of such enclosed teeth upon desired biting action by the patient.

Referring back to FIG. 3, another advantage of appliance 10 of the present invention is shown by the fact that soft, persistently resilient region 16 provides for improved retention of jacketed teeth such as tooth 22 by extending apically to what are known as the undercuts of the tooth. Conventional hard splints cannot extend apically to the undercuts, and conventional "soft" splints are only able to extend to the undercuts before they eventually harden, at which point such extension is impossible.

Referring to FIGS. 3-4, it should also be understood that the exact number of zones 28 formed in a given area of region 16 may vary. To achieve the desired precise vertical and lateral positioning of the mandible described above, appliance 10 must be formed with at least three such zones, two being located substantially distally from the sagittal plane and one being located substantially mesially from the sagittal plane. For example, referring back to FIG. 1, such a requirement would necessitate forming two zones in region 16 adjacent teeth 34, 36 that are distal to the sagittal plane (represented by dashed line 38) and one zone adjacent tooth 40 that is mesial to the sagittal plane.

Referring to FIGS. 2A-2B, it should be apparent that the applicance of the present invention may be constructed with expanse 18 having substantially planar second surface 18b (FIG. 2A) or with expanse 118 having second surface 118b that conforms generally to the cusps of a desired set of teeth such as the lower teeth. The latter embodiment results in a splint that is usable as a so-called anatomical splint, or repositioning splint, which is used to do what is known as "recapture the disk" associated with the TMJ. The former embodiment is for splints that are to be used as relaxation or stabilization splints.

Accordingly, while a preferred embodiment of the invention has been described herein, it is appreciated that modifications are possible that are within the scope of the invention.

It is claimed and desired to secure by letters patent:

1. A soft, persistently resilient interocclusal dental appliance, comprising:
   a body made from an injectable, curable composition, with the composition including a polymer component consisting essentially of butyl methacrylate polymer, a monomer component consisting essentially of butyl methacrylate monomer and an effective amount of polymerizing agent.

2. The appliance of claim 1 wherein the polymer component is about 20-80% by volume of it.

3. The appliance of claim 2 being formed into a temporo-mandibular joint dysfunction appliance.

4. The appliance of claim 2 being formed into an anti-snoring device.

5. A soft, persistently resilient interocclusal dental appliance, comprising:
   a body made from an injectable, curable composition, with the composition including a polymer component made substantially of butyl methacrylate polymer, a monomer component made substantially of butyl methacrylate monomer, and an effective amount of polymerizing agent.

6. The appliance of claim 5 wherein the polymer component is about 20-80% by volume of it.

7. The appliance of claim 6 being formed into a temporo-mandibular joint dysfunction appliance.

8. The appliance of claim 6 being formed into an anti-snoring device.

9. A soft, persistently resilient interocclusal dental appliance, comprising:
   a body made from a curable composition, with the composition including a polymer component made substantially of butyl methacrylate polymer, a monomer component made substantially of butyl methacrylate monomer and an effective amount of polymerizing agent.

10. The appliance of claim 9 wherein the polymer component is about 20-80% by volume of it.

11. The appliance of claim 10 being formed into a temporo-mandibular joint dysfunction appliance.

12. The appliance of claim 10 being formed into an anti-snoring device.

13. A soft, persistently resilient, plural-material, interocclusal dental appliance, comprising:
   a body including a hard region and a soft region, the soft region being made from a curable composition that includes a polymer component made substantially of butyl methacrylate polymer, a monomer component made substantially of butyl methacrylate monomer, an effective amount of polymerizing agent, and with the soft region formed from the composition being bondable to the hard region.

14. The appliance of claim 13 wherein the polymer component is about 20-80% by volume of it.

15. The appliance of claim 13 being formed into a temporo-mandibular joint dysfunction appliance.

16. The appliance of claim 13 being formed into an anti-snoring device.

17. An injectable, curable composition for making a soft, persistently resilient interocclusal dental appliance, comprising:
- a polymer component consisting essentially of butyl methacrylate polymer;
- a monomer component consisting essentially of butyl methacrylate monomer;
- an effective amount of polymerizing agent; and
- with the composition being sufficiently liquid to allow it to be injectable.

18. The composition of claim 17 wherein the polymer component is about 20-80% by volume of it.

19. An injectable, curable composition for making a soft, persistently resilient interocclusal dental appliance, comprising:
- a polymer component made substantially of butyl methacrylate polymer;
- a monomer component made substantially of butyl methacrylate monomer;
- an effective amount of polymerizing agent; and
- with the composition being sufficiently liquid to allow it to be injectable.

20. The composition of claim 19 wherein the polymer component is about 20-80% by volume of it.

21. An injectable, curable composition for making a soft, persistently resilient region of a plural-material, interocclusal dental appliance, which appliance also includes a hard region, comprising:
- a polymer component made substantially of butyl methacrylate polymer;
- a monomer component made substantially of butyl methacrylate monomer;
- an effective amount of polymerizing agent; and
- with the composition being bondable to the hard region.

22. The composition of claim 21 wherein the polymer component is about 20-80% by volume of it.

* * * * *